(12) United States Patent
Song et al.

(10) Patent No.: US 10,653,360 B2
(45) Date of Patent: May 19, 2020

(54) SYSTEM AND METHOD OF DIRECTING BIOSIGNAL DETECTOR ARRANGEMENT

(71) Applicant: Daegu Gyeongbuk Institute of Science and Technology, Daegu (KR)

(72) Inventors: Chanho Song, Busan (KR); Sangseo Jeon, Wonju-si (KR); Jaesung Hong, Daegu (KR)

(73) Assignee: Daegu Gyeongbuk Institute of Science and Technology, Daegu (KR)

( * ) Notice: Subject to any disclaimer, the term of this patent is extended or adjusted under 35 U.S.C. 154(b) by 257 days.

(21) Appl. No.: 15/588,731

(22) Filed: May 8, 2017

(65) Prior Publication Data

US 2018/0103904 A1 Apr. 19, 2018

(30) Foreign Application Priority Data

Oct. 18, 2016 (KR) .......................... 10-2016-0135186

(51) Int. Cl.
*A61B 5/00* (2006.01)
*A61B 5/0478* (2006.01)
*A61B 5/107* (2006.01)

(52) U.S. Cl.
CPC ............ *A61B 5/684* (2013.01); *A61B 5/0478* (2013.01); *A61B 5/1077* (2013.01); *A61B 5/6803* (2013.01); *A61B 5/742* (2013.01)

(58) Field of Classification Search
None
See application file for complete search history.

(56) References Cited

U.S. PATENT DOCUMENTS

| 6,238,338 B1* | 5/2001 | DeLuca | A61B 5/681 128/903 |
| 2008/0275359 A1* | 11/2008 | Mintz | A61B 5/0476 600/544 |
| 2009/0012402 A1* | 1/2009 | Mintz | A61B 5/0008 600/473 |

(Continued)

FOREIGN PATENT DOCUMENTS

| JP | 2011-502647 | 1/2011 |
| JP | 4968167 | 7/2012 |
| KR | 10-2016-0023487 | 3/2016 |

OTHER PUBLICATIONS

R.Selvarasu, Implementation of Portable Device for Real Time Bio Signal Analysis using LabVIEW, 7 pages, Jan. 2015.*

(Continued)

*Primary Examiner* — Tung S Lau

(57) ABSTRACT

Disclosed is a system and method of directing a biosignal detector arrangement. The system for directing a biosignal detector arrangement may include a biosignal detector configured to detect a biosignal of an object, a measurer configured to obtain, in real-time, information including surface data of the object and position data associated with an arrangement of the biosignal detector relative to the object based on the surface data, a processor configured to set initially obtained information of the obtained information as reference information for a surface registration and compare the reference information to finally obtained information of the obtained information, and a display configured to display the reference information and the finally obtained information.

15 Claims, 5 Drawing Sheets

(56) References Cited

U.S. PATENT DOCUMENTS

2015/0351655 A1* 12/2015 Coleman ............... A61B 5/742
600/301

OTHER PUBLICATIONS

Maria Hakonena, Current state of digital signal processing in myoelectric interfaces and related applications, Mar. 7, 2015, 26 pages.*

ErickaJanetRechy-Ramirez, Bio-signal basedcontrolinassistiverobots: a survey, Mar. 17, 2015, 17 pages.*

Clemens Amon, Design and Evaluation of an EMG-based Recording and Detection System, Jun. 2013, 54 pages.*

M. B. I. Reaz, Techniques of EMG signal analysis: detection, processing, classification and applications, Jan. 18, 2006, 25 pages.*

Jonghwa Kim, Stephan Mastnik, EMG-based Hand Gesture Recognition for Realtime Biosignal Interfacing, Jan. 13-16, 2008, 10 pages.*

Rubana H. Chowdhury, Surface Electromyography Signal Processing and Classification Techniques, Sep. 17, 2013, 36 pages.*

Nurhazimah Nazmi, A Review of Classification Techniques of EMG Signals during Isotonic and Isometric Contractions, Aug. 17, 2016, 28 pages.*

Fabian J. Theis, Biomedical signal analysis: contemporary methods and applications, 2010 Massachusetts Institute of Technology, 28 pages (Year: 2010).*

Gregory R. Bashford, Ultrasound Three-Dimensional Velocity Measurements by Feature Tracking, Biomedical Imaging and Biosignal Analysis Laboratory, 10 pages (Year: 1996).*

Song et al. "Markerless Augmented Reality-Based Navigation for Precise Electrode Positioning", The 12th Asian Conference on Computer Aided Surgery, ACCAS 2016, Daejeon, Korea, Oct. 14-15, 2016, Program of Technical Session, 24 P., Oct. 15, 2016.

Song et al. "Markerless Augmented Reality-Based Navigation for Precise Electrode Positioning", The Sector Union Conference of Society for Computational Design and Engineering, Poster Sessions, Korea, Aug. 25-26, 2016, 11 P., Aug. 25, 2016.

* cited by examiner

SYSTEM AND METHOD OF DIRECTING BIOSIGNAL DETECTOR ARRANGEMENT

RELATED APPLICATION

This application claims the benefit of priority of Korean Patent Application No. 10-2016-0135186 filed Oct. 18, 2016, the contents of which are incorporated herein by reference in their entirety.

FIELD AND BACKGROUND OF THE INVENTION

One or more example embodiments relate to a system and method of directing a biosignal detector arrangement.

In a study for which a change is observed over a long period of time, that is, a longitudinal study, whether an arrangement of a biosignal detector, for example, a probe and an electrode, configured to detect a biosignal is reproduced may be significant. A test-retest reliability may be guaranteed by rearranging a probe at an identical position in a medium-term and long-term study.

There is a 10-20 system that allows an arrangement of a biosignal detector to be reproduced. With the 10-20 system, the biosignal detector may be arranged using an anatomical feature point, for example, a nasion, an inion, and a pre-auricular point. However, errors may occur in a process of recognizing or measuring the anatomical feature point.

For example, Japanese Patent Laid-Open Publication No. 2011-502647 discloses a method and apparatus for performing electroencephalography.

SUMMARY OF THE INVENTION

An aspect provides a system and method of directing a biosignal detector arrangement that may display a position of a biosignal detector configured to detect a biosignal relative to an object based on surface data of the object without using an optical sensor.

Another aspect provides a system and method of directing a biosignal detector arrangement that may visualize and overlap an initial position of a biosignal detector and a position of the biosignal detector obtained in real-time through an augmented reality (AR) technology.

According to an aspect, there is provided a system for directing a biosignal detector arrangement including a biosignal detector configured to detect a biosignal of an object, a measurer configured to obtain, in real-time, information including surface data of the object and position data associated with an arrangement of the biosignal detector relative to the object based on the surface data, a processor configured to set initially obtained information of the obtained information as reference information for a surface registration and compare the reference information to finally obtained information of the obtained information, and a display configured to display the reference information and the finally obtained information.

The processor may be configured to extract the surface data of the object and the position data associated with the arrangement of the biosignal detector from the information obtained by the measurer.

The processor may be configured to set initially obtained surface data of the extracted surface data as reference surface data of the reference information, and set initially obtained position data of the extracted position data as reference position data of the reference information.

The processor may be configured to perform registration on the reference surface data and the surface data of the finally obtained information.

The display may be configured to display the reference position data and finally obtained position data of the finally obtained information based on the reference surface data and the surface data on which the registration is performed.

The display may be configured to display the reference position data as a feature point that is emitted to a user.

The processor may be configured to separate the position data associated with the arrangement of the biosignal detector and the surface data of the object from the information obtained by the measurer.

According to an aspect, there is provided a method of directing a biosignal detector arrangement including preprocessing data used to obtain information including surface data of an object and position data associated with an arrangement of a biosignal detector configured to detect a biosignal of the object relative to the object, and set the surface data as reference surface data and the position data as reference position data from the information, iteratively processing data used to obtain information including real-time surface data of the object and real-time position data associated with the arrangement of the biosignal detector relative to the object and perform registration on the reference surface data and the real-time surface data, the data having been subsequently preprocessed, and displaying the reference position data based on the reference surface data and the real-time surface data on which the registration is performed.

The preprocessing may include separating the surface data and the position data obtained by preprocessing the data from the obtained information.

The displaying may include displaying the reference position data as a feature point that is emitted to a user.

Additional aspects of example embodiments will be set forth in part in the description which follows and, in part, will be apparent from the description, or may be learned by practice of the disclosure.

BRIEF DESCRIPTION OF THE SEVERAL VIEWS OF THE DRAWINGS

These and/or other aspects, features, and advantages of the invention will become apparent and more readily appreciated from the following description of example embodiments, taken in conjunction with the accompanying drawings of which.

DESCRIPTION OF SPECIFIC EMBODIMENTS OF THE INVENTION

Figure 1:
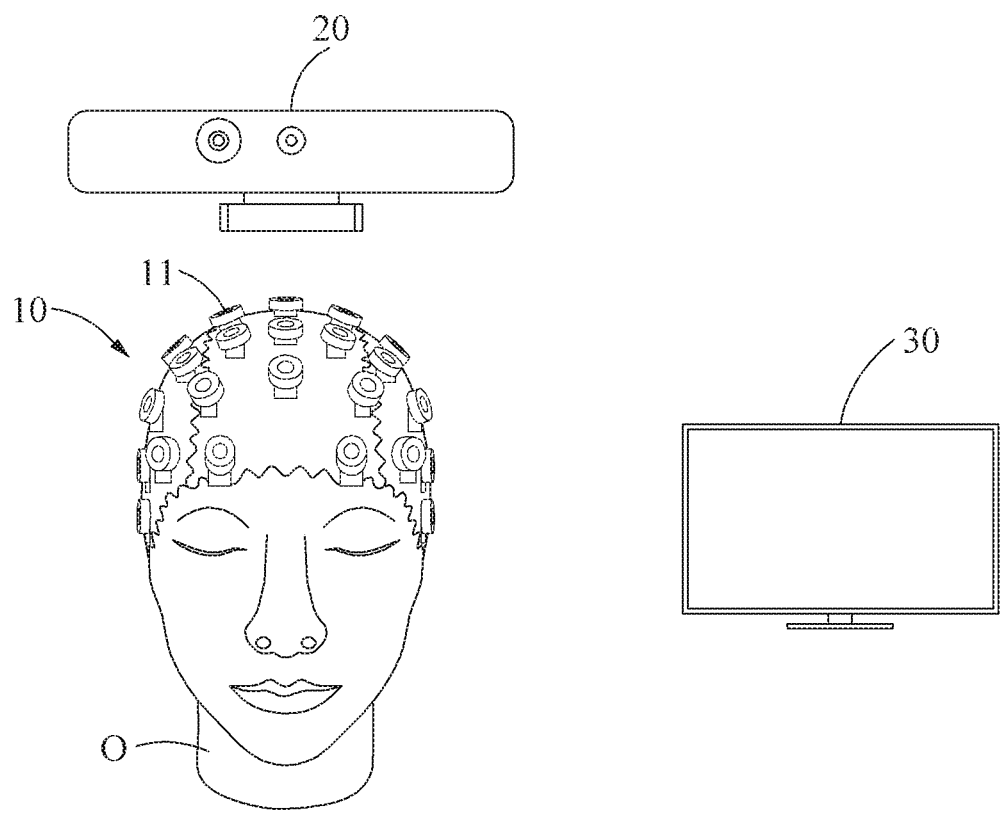
FIG. 1 illustrates a system for directing a biosignal detector arrangement according to an example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

Hereinafter, example embodiments will be described in detail with reference to the accompanying drawings. The scope of the right, however, should not be construed as limited to the example embodiments set forth herein. Regarding the reference numerals assigned to the elements in the drawings, it should be noted that the same elements will be designated by the same reference numerals.

FIG. 1 illustrates a system for directing a biosignal detector arrangement according to an example embodiment.

Referring to FIG. 1, a system 1 for directing the biosignal detector arrangement includes a biosignal detector 10, a measurer 20, a processor (not shown), and a display 30.

A biosignal is a form of an electric potential or a current occurring in nerve cells or muscular cells of an object. The biosignal may be obtained by analyzing and collecting a change in an electrical signal, for example, an electroencephalogram (EEG), detected through the biosignal detector 10, for example, an electrode or a probe attached to a body of the object.

The biosignal detector 10 may be arranged and used by the object. The object may include, for example, a person and an animal. Herein, the object is described as a person as an example.

The biosignal detector 10 detects a biosignal of an object O. The biosignal detector 10 includes a detecting member 11 configured to detect the biosignal of the object O. A plurality of detecting members including, for example, the detecting member 11, may be formed on a surface of the biosignal detector 10. For example, the detecting member 11 corresponds to an electrode or a probe configured to detect the biosignal of the object O and detects the EEG when the biosignal detector 10 is disposed on a scalp of the person.

The measurer 20 obtains, in real-time, information including surface data of the object O and position data associated with an arrangement of the biosignal detector 10 relative to the object O based on the surface data.

The surface data is obtained by converting surfaces of the object O to data by the measurer 20. The measurer 20 may store the converted surfaces of the object O in a form of three-dimensional (3D) data, for example, a point cloud.

The position data is obtained by converting, to data, a position at which the biosignal detector 10 is arranged relative to the object O based on the surface data by the measurer 20. The measurer 20 may store the converted position at which the biosignal detector 10 is arranged relative to the object O based on the surface data in a form of 3D data.

The measurer 20 may be disposed toward the biosignal detector 10 disposed on the object O. The measurer 20 may scan positions of a plurality of detecting members including the detecting member 11 relative to the object O formed on the surface of the biosignal detector 10. The measurer 20 may store the positions of the detecting members including the detecting member 11 to be scanned. For example, the measurer 20 is a Red, Green, Blue, Distance (RGB-D) camera using an RGB-D sensor.

The processor may set initially obtained information of the obtained information including the surface data and the position data as reference information for a surface registration and compare the reference information to finally obtained information of the obtained information.

The surface registration may involve matching one surface to another surface. In detail, through calibration, the surface registration may involve matching coordinates on one surface to coordinates on another surface. For example, one surface and another surface may be matched through the surface registration and then the surfaces may be processed as reference surfaces for processing the data when another data process is required.

Because the information including the surface data and the position data is obtained by the measurer 20 in real-time, a unique time value may be assigned to the information. For example, initially obtained surface data and position data or finally obtained surface data and position data may be included in the information including the surface data and the position data.

Thus, the processor may set the initially obtained information of the information obtained by the measurer 20 as reference information for the surface registration to subsequently process the data. Also, the processor may compare the set reference information to the finally obtained information of the information obtained by the measurer 20. Detailed descriptions of a method of comparing the set reference information to the finally obtained information of the information obtained by the measurer 20 will be provided with reference to FIGS. 2 through 4.

The display 30 displays the reference information and the finally obtained information. That is, the display 30 displays the initially obtained information and the finally obtained information of the information obtained by the measurer 20. In relation to the processor, detailed descriptions of a method of displaying the initially obtained information and the finally obtained information of the information obtained by the measurer 20 will be provided with reference to FIGS. 2 and 4.

Figure 2:
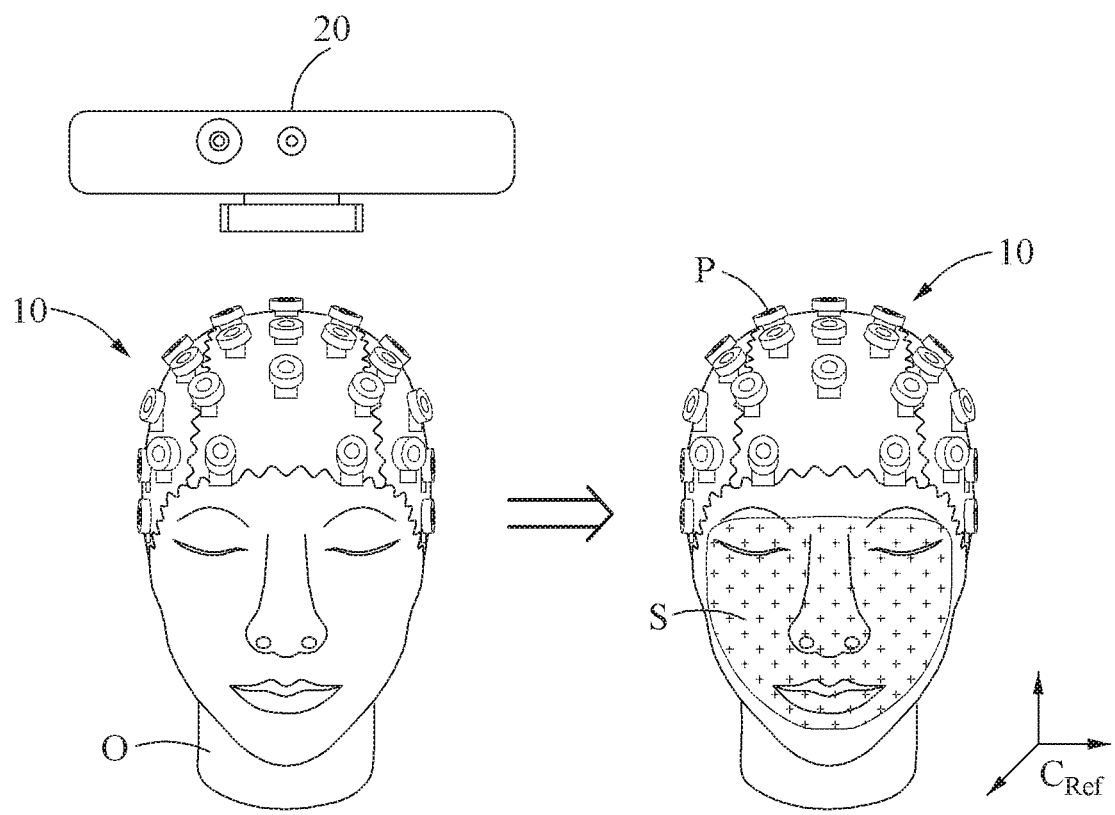
FIG. 2 illustrates a method by which a system for directing a biosignal detector arrangement initially obtains surface data and position data according to an example embodiment.
Figure 3:
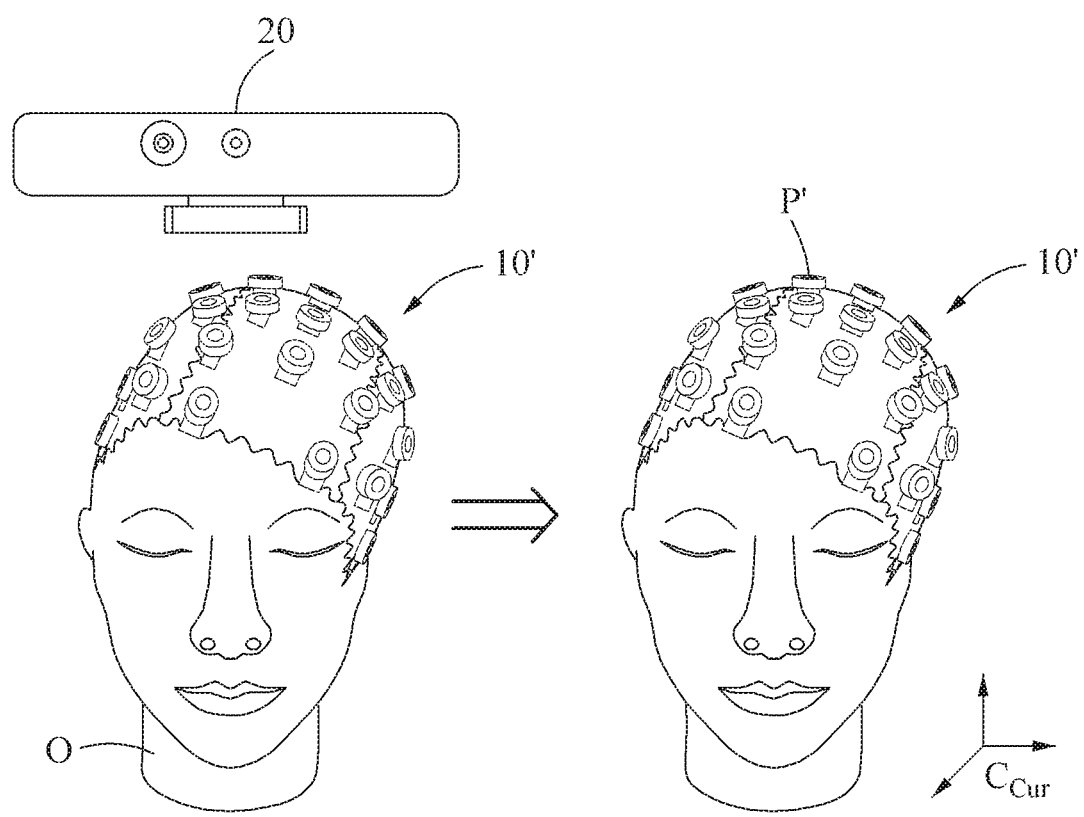
FIG. 3 illustrates a method by which a system for directing a biosignal detector arrangement obtains, in real-time, surface data and position data according to an example embodiment.
Figure 4:
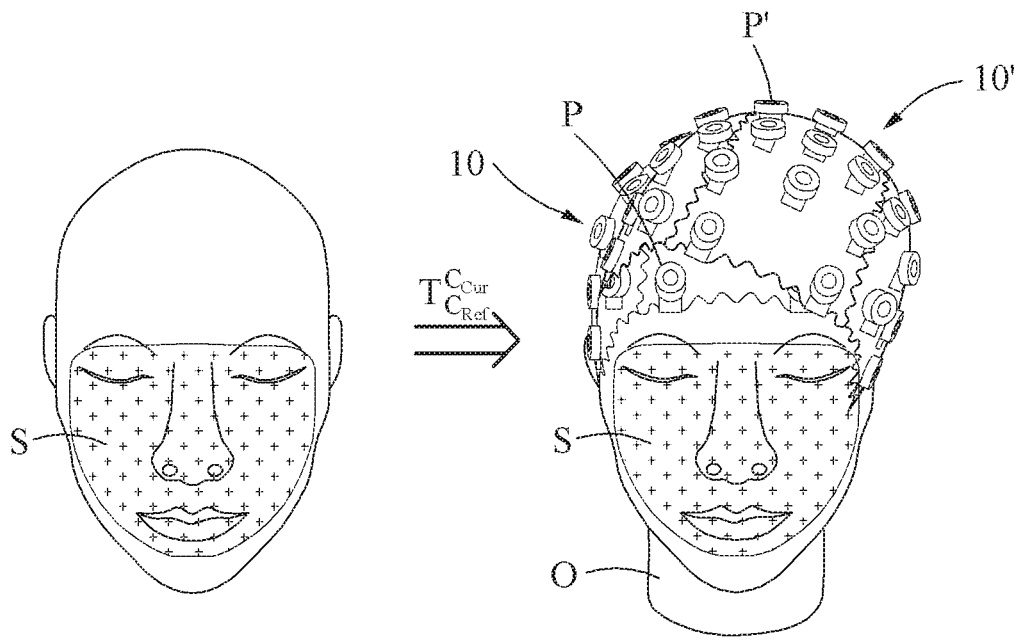
FIG. 4 illustrates a method of comparing initially obtained surface data and position data to surface data and position data obtained in real-time according to an example embodiment.

FIG. 2 illustrates a method by which a system for directing a biosignal detector arrangement initially obtains surface data and position data according to an example embodiment. FIG. 3 illustrates a method by which a system for directing a biosignal detector arrangement obtains, in real-time, surface data and position data according to an example embodiment. FIG. 4 illustrates a method of comparing initially obtained surface data and position data to surface data and position data obtained in real-time according to an example embodiment.

FIG. 2 illustrates an example in which surface data S of the object O and position data P associated with an arrangement of the biosignal detector 10 relative to the object O are initially obtained by the measurer 20 when the biosignal detector 10 is initially arranged relative to the object O. In this case, initially obtained information of information including the surface data S of the object O and the position data P associated with the arrangement of the biosignal detector 10 relative to the object O may be processed by the processor.

In detail, the processor may extract each of the surface data S of the object O and the position data P associated with the arrangement of the biosignal detector 10 from the information obtained by the measurer 20. The extracted surface data S may be set as reference surface data for a surface registration and the extracted position data P may be displayed by the display 30.

The processor may set the initially obtained surface data S of the information obtained by the measurer 20 as the reference surface data of the reference information and set the initially obtained position data P of the information obtained by the measurer 20 as the reference position data of the reference information. That is, the initially obtained surface data S may be set as the reference surface data such that the surface registration is performed on the initially obtained surface data S and surface data to be measured in real-time, and the initially obtained position data P may be set as the reference position data to be compared with position data to be measured in real-time.

The display 30 displays the surface data S and the position data P as feature points that are emitted to a user. Thus, the user may visualize and easily know an initial position of the biosignal detector 10 relative to the object O.

FIG. 3 illustrates an example in which a biosignal detector 10' is rearranged relative to the object O according to user requirements after the biosignal detector 10 is initially arranged relative to the object O. In this case, information including surface data (not shown) of the object O and position data V associated with an arrangement of the biosignal detector 10' relative to the object O may be measured by the measurer 20 in real-time. The processor may extract the finally obtained surface data and the finally obtained position data V of the information measured in real-time.

FIG. 4 illustrates an example in which the measurer 20 compares initially obtained information to finally obtained information.

The processor may compare the initially obtained information set as reference information for a surface registration to the finally obtained information.

In detail, the processor may perform the surface registration on the surface data S of the finally obtained information and reference surface data S of the reference information. That is, the processor may compare, in real-time, reference position data P associated with a subsequent arrangement of the biosignal detector 10, for example, to the finally obtained position data V by matching coordinates of the reference surface data S of the reference information and coordinates of the surface data S of the finally obtained information.

The display 30 may display the reference position data P and the position data P' of the finally obtained information based on the surface data S and the reference surface data S on which the surface registration is performed. That is, the display 30 may show that the reference position data P is compared to the position data P' of the finally obtained information while the surface data S is fixed.

In addition, the display 30 may display the reference position data P as a feature point that is emitted to the user. For example, the reference position data P is displayed by displaying the initially obtained position data P as an emitted feature point without displaying the position data P' of the finally obtained information and thus, the display 30 allows the user to dispose the biosignal detector 10' relative to the object O at a position at which the biosignal detector 10 was disposed relative to the object O. Thus, when the user conducts a longitudinal study, the biosignal detectors 10 and 10' are arranged relative to the object O in a way that achieves reproducibility such that a test-retest reliability may be guaranteed. Also, the user may match the reference position data P and the position data P' of the finally obtained information such that predetermined positions of detecting members of the biosignal detectors 10 and 10' are always maintained and an error of an anatomical feature point is reduced.

Figure 5:
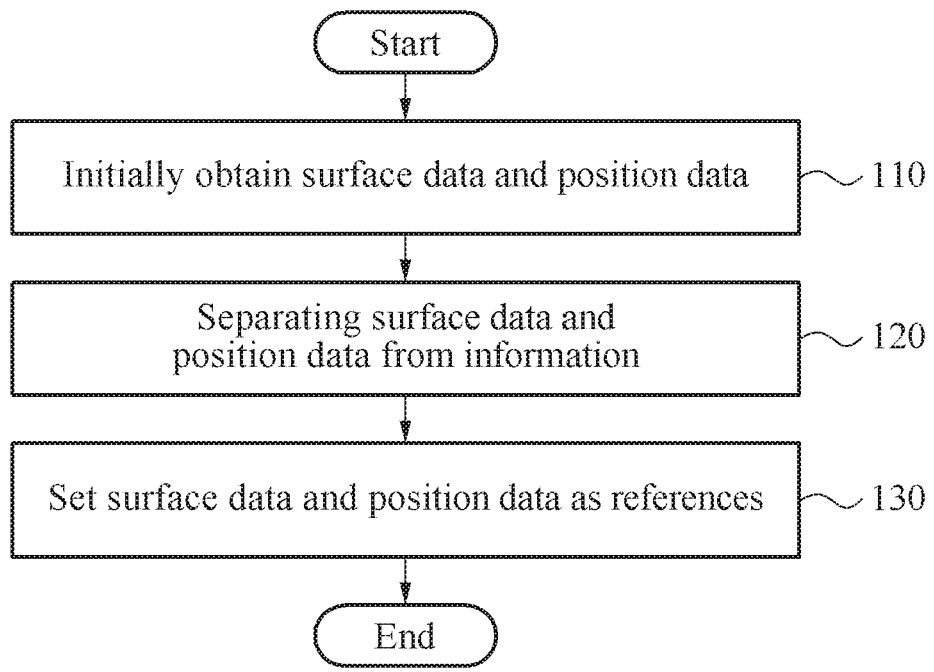
FIG. 5 is a flowchart illustrating an operation of preprocessing data in a method of directing a biosignal detector arrangement according to an example embodiment.
Figure 6:
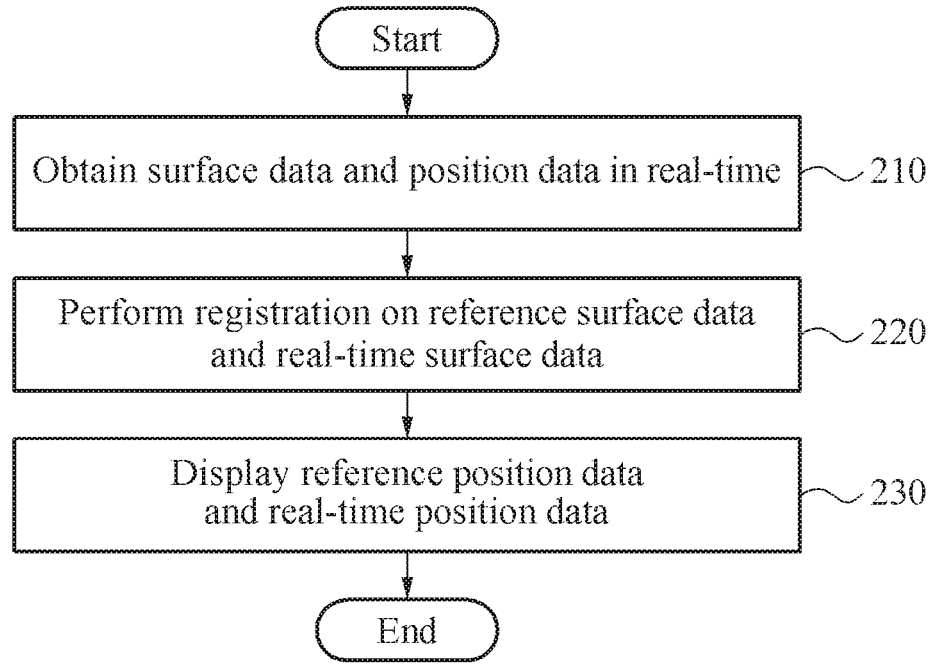
FIG. 6 is a flowchart illustrating an operation of iteratively processing data in a method of directing a biosignal detector arrangement according to an example embodiment.

Detailed description of a method of directing a bio signal detector arrangement is provided with reference to FIGS. 5 and 6.

The method of directing the biosignal detector arrangement may include an operation of preprocessing data, an operation of iteratively processing data, and an operation of displaying data.

FIG. 5 is a flowchart illustrating the operation of preprocessing the data in the method of directing the biosignal detector arrangement when the biosignal detector configured to detect a biosignal is initially arranged relative to an object in a longitudinal study.

Referring to FIG. 5, the operation of preprocessing the data includes operation 110 of initially obtaining surface data and position data, operation 120 of separating the surface data and the position data from the obtained information, and operation 130 of setting the surface data and the position data as references.

Operation 110 of initially obtaining the surface data and the position data includes an operation of obtaining the information including the surface data of an object and the position data associated with the arrangement of the biosignal detector configured to detect the biosignal of the object relative to the object. In this case, the obtained information may be stored in a processor.

Operation 120 of separating the surface data and the position data from the obtained information includes an operation of separating the surface data and the position data from the information including the obtained surface data and the obtained position data.

Operation 130 of setting the surface data and the position data as the references includes an operation of setting the surface data as reference surface data and the position data as reference position data from the information including the obtained surface data and the obtained position data. A surface registration is to be performed on the set reference surface data and surface data obtained in real-time in response to the biosignal detector being rearranged relative to the object when a re-test is subsequently performed. When the re-test is subsequently performed, the set reference position data is to be compared with the position data obtained in real-time after the surface registration is performed.

FIG. 6 is a flowchart illustrating an operation of iteratively processing data in a method of directing a biosignal detector arrangement when a biosignal detector configured to detect a biosignal is iteratively arranged relative to an object for a number of operations in a longitudinal study.

The operation of iteratively processing the data includes operation 210 of obtaining surface data and position data in real-time, operation 220 of performing a registration on reference surface data and real-time surface data, and operation 230 of displaying the reference position data and the real-time position data.

Operation 210 of obtaining the surface data and the position data in real-time is performed after the operation of preprocessing the data is performed.

Operation 210 of obtaining the surface data and the position data in real-time includes an operation of obtaining information including the real-time surface data of the object and real-time position data associated with the arrangement of the biosignal detector relative to the object. In this case, the obtained information may be stored in a processor.

Operation 220 of performing the registration on the reference surface data and the real-time surface data includes an operation of comparing the reference surface data set in the operation of preprocessing the data to the real-time surface data of the object obtained in real-time and matching coordinates of the reference surface data and coordinates of the real-time surface data.

Operation 230 of displaying the reference position data and the real-time position data includes an operation of displaying the reference position data based on the reference surface data and the real-time surface data on which the registration is performed. The reference position data may be displayed as a feature point that is emitted to the user. In this case, the user may rearrange the biosignal detector at a position at which the biosignal detector was disposed based on the reference position data displayed as an emitted feature point.

According to an aspect, a system and method of directing a biosignal detector arrangement may have an advantage of displaying a position of a biosignal detector configured to detect a biosignal relative to an object based on surface data of the object without using an optical sensor, an advantage of visualizing and overlapping an initial position of the biosignal detector and a position of the biosignal detector obtained in real-time through an augmented reality (AR) technology, or an advantage of guaranteeing a test-retest reliability by coherently rearranging the biosignal detector at an identical position in a way that achieves reproducibility in a longitudinal study.

According to another aspect, an effect of a system and method of directing a biosignal detector arrangement is not limited by above-mentioned descriptions and other effects may be understood by those skilled in the art from the description.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A system for guaranteeing test-retest reliability by ensuring identical placement of a plurality of biosignal detectors in repeated re-arrangement of the plurality of biosignal detectors, the system comprising:
    a plurality of biosignal detectors configured to detect at least one biosignal of an object;
    a measurer configured to obtain, in real-time, information including surface data of the object and position data associated with a placement arrangement of the plurality of biosignal detectors relative to the object, based on the surface data, said surface data describing a three dimensional (3D) structure of a certain surface of said object, wherein said placement arrangement describing a position of each of said plurality of biosignal detectors on said certain surface;
    a processor configured to set a first information obtained from said measurer as reference information for a surface registration and compare the reference information to a second information obtained from said measurer; wherein said first information is associated with a first placement arrangement of said plurality of biosignal detectors on said surface of said object and wherein said second information is associated with a second placement arrangement of said plurality of biosignal detectors on said surface of said object, said second placement arrangement is a subsequent re-arrangement conducted following said first placement arrangement being an initial placement arrangement; and
    a display configured to display the reference information and the second obtained information to guarantee test-retest reliability by ensuring identical placement arrangement by visualizing an overlap between said first placement arrangement and said second placement arrangement.

2. The system of claim 1, wherein the processor is configured to extract the surface data of the object and the position data associated with the placement arrangement of the plurality of biosignal detectors from the information obtained by the measurer.

3. The system of claim 1, wherein the processor is configured to separate the position data associated with the placement arrangement of the plurality of biosignal detectors and the surface data of the object from the information obtained by the measurer.

4. The system of claim 1, wherein said plurality of biosignal detectors are disposed on a scalp of a person.

5. The system of claim 1, wherein said measurer is configured to store a conversion of said surface of said object in a three-dimensional (3D) data format.

6. The system of claim 1, wherein said measurer is a camera.

7. The system of claim 1, wherein said information including unique time value indicative of a time of directing said placement arrangement.

8. The system of claim 1, wherein said measurer obtains said information by scanning positions of said plurality of biosignal detectors.

9. The system of claim 1, wherein said processor compares the reference information to the second information by matching coordinates of the surface data.

10. The system of claim 2, wherein the processor is configured to set a first obtained surface data of the extracted surface data as reference surface data of the reference information, and to set a first obtained position data of the extracted position data as reference position data of the reference information.

11. The system of claim 5, wherein said 3D data format is a point cloud.

12. The system of claim 6, wherein said camera is a Red, Green, Blue, Distance (RGB-D) camera using an RGB-D sensor.

13. The system of claim 10, wherein the processor is configured to perform registration on the reference surface data and the surface data of the second obtained information.

14. The system of claim 13, wherein the display is configured to display the reference position data and the second obtained position data of the second obtained information based on the reference surface data and the surface data on which the registration is performed.

15. The system of claim 14, wherein the display is configured to display the reference position data as a feature point that is emitted to a user.

\* \* \* \* \*